United States Patent
Banerjee et al.

(10) Patent No.: US 9,670,522 B2
(45) Date of Patent: Jun. 6, 2017

(54) QUANTITATIVE ACOUSTIC CONTRAST TOMOGRAPHY FOR STUDYING FUNGAL GROWTH AND TOXICITY

(71) Applicants: Sourav Banerjee, Irmo, SC (US); Anindya Chanda, Lexington, SC (US)

(72) Inventors: Sourav Banerjee, Irmo, SC (US); Anindya Chanda, Lexington, SC (US)

(73) Assignee: University of South Carolina, Columbia, SC (US)

( * ) Notice: Subject to any disclaimer, the term of this patent is extended or adjusted under 35 U.S.C. 154(b) by 204 days.

(21) Appl. No.: 14/592,368

(22) Filed: Jan. 8, 2015

(65) Prior Publication Data

US 2015/0192674 A1   Jul. 9, 2015

Related U.S. Application Data

(60) Provisional application No. 61/924,928, filed on Jan. 8, 2014.

(51) Int. Cl.
  *G01N 29/34* (2006.01)
  *G01N 29/46* (2006.01)
  (Continued)

(52) U.S. Cl.
  CPC ........... *C12Q 1/04* (2013.01); *G01N 29/0681* (2013.01); *G01N 29/221* (2013.01);
  (Continued)

(58) Field of Classification Search
  CPC .... C12Q 1/04; G01N 29/0681; G01N 29/343; G01N 29/46; G01N 29/221;
  (Continued)

(56) References Cited

U.S. PATENT DOCUMENTS 4,459,852 A * 7/1984 Chubachi ............... G01H 3/125
  73/606
4,615,591 A * 10/1986 Smith ..................... G12B 1/00
  248/576

(Continued)

OTHER PUBLICATIONS

Bastmeyer, et al., "Force exertion in fungal infection," *Annu Rev Biophys Biomol Struct* 31, 321 (2002), pp. 321-341.

(Continued)

*Primary Examiner* — J M Saint Surin (74) *Attorney, Agent, or Firm* — Dority & Manning, P.A.

(57) ABSTRACT

Methods for ultrasonically imaging a heterogeneous 3D-cell population without physically probing are provided. The method can comprises: pulsing ultrasound waves having a wave frequency of about 10 MHz to about 2 GHz through a lens rod, wherein the lens rod focuses the ultrasound waves onto the cell population via a concave lens-head (e.g., comprising sapphire), and wherein the cell population is positioned on the reflective surface such that the ultrasound waves are reflected back to the lens-head; receiving the reflected waves through the lens head and the lens rod at a signal receiver; scanning the lens-head across multiple points in the x,y plane; and at each point in the x,y plane, moving the lens-head in a z-direction such that a signal is received at multiple intervals in the z-direction for each point in the x,y plane.

13 Claims, 4 Drawing Sheets

(51) Int. Cl.
| | |
|---|---|
| G01N 29/06 | (2006.01) |
| G01N 29/22 | (2006.01) |
| G01S 15/89 | (2006.01) |
| G01S 7/52 | (2006.01) |
| C12Q 1/04 | (2006.01) |
| A61B 8/14 | (2006.01) |
| A61B 8/00 | (2006.01) |
| A61B 8/08 | (2006.01) |

(52) U.S. Cl.
CPC ........... *G01N 29/343* (2013.01); *G01N 29/46* (2013.01); *G01S 7/52079* (2013.01); *G01S 15/8936* (2013.01); *G01S 15/8956* (2013.01); *G01S 15/8993* (2013.01); *A61B 8/14* (2013.01); *A61B 8/44* (2013.01); *A61B 8/483* (2013.01)

(58) Field of Classification Search
CPC ............. G01S 15/8956; G01S 15/8993; G01S 15/8936; G01S 7/52079; A61B 8/14; A61B 8/44; A61B 8/483
USPC .......................................................... 73/606
See application file for complete search history.

(56) References Cited

U.S. PATENT DOCUMENTS

| | | | | |
|---|---|---|---|---|
| 5,738,677 | A * | 4/1998 | Colvard | A61F 9/00802 128/898 |
| 5,846,638 | A * | 12/1998 | Meissner | B32B 17/00 117/1 |
| 7,630,148 | B1 * | 12/2009 | Yang | A61B 1/00096 359/664 |
| 2008/0228073 | A1 | 9/2008 | Silverman | A61B 5/0066 600/437 |
| 2012/0234625 | A1 * | 9/2012 | Laugharn, Jr. | G10K 11/28 181/140 |

OTHER PUBLICATIONS

Howard, et al.; "Penetration of hard substrates by a fungus employing enormous turgor pressures," *Proc Natl Acad Sci USA* 88, 11281 (Dec. 15, 1991) (5 pages).
Bates, et al.; "Multicolor super-resolution imaging with photo-switchable fluorescent probes," *Science* 317, 1749 (Sep. 21, 2007) (6 pages).
Betzig, et al.; "Imaging intracellular fluorescent proteins at nanometer resolution," *Science* 313, 1642 (Sep. 15, 2006) (5 pages).
Willig, et al.; "STED microscopy with continuous wave beams," *Nat Methods* 4, 915 (Nov. 2007).
Serrano, et al.; "Fine needle aspiration cytology of metastatic hepatic adrenocortical carcinoma mimicking hepatocellular carcinoma: a case report," *Acta Cytol* 45, 768 (Sep.-Oct. 2001) (3 pages).
Valberg "Cytoplasmic motions, rheology, and structure probed by a novel magnetic particle method," *J Cell Biol* 101, 130 (Jul. 1985) (11 pages).
Mackay, "Measuring the elastic properties of living cells with atomic force microscopy indentation," *Methods Mol Biol* 931, 313 (2013) (17 pages).
Radmacher, "Measuring the elastic properties of biological samples with the AFM. IEEE Eng Med," *Biol Mag* 16, 47 (Mar.-Apr. 1997).
Kundu, et al.; "Acoustic microscope lens modeling and its application in determining biological cell properties from single- and multi-layered cell models," *J Acoust Soc Am* 120, 1646 (Sep. 2006) (10 pages).
Kundu et al.; "Cell property determination from the acoustic microscope generated voltage versus frequency curves," *Biophys J* 78, 2270 (May 2000) (10 pages).
Hildebrand, et al; "Acoustic microscopy of living cells," *Proc Natl Acad Sci U S A* 78, 1656 (Mar. 1981) (5 pages).
Weiss, et al.; "Mechanical properties of single cells by high-frequency time-resolved acoustic microscopy," *IEEE Trans Ultrason Ferroelectr Freq Control* 54, 2257 (Nov. 2007) (15 pages).
Jürgen, et al.; "Ultrasonic Nondestructive Evaluation," (CRC Press, 2003).
Bertrand et al., "Detection of metabolite induction in fungal co-cultures on solid media by high-throughput differential ultra-high pressure liquid chromatography-time-of-flight mass spectrometry fingerprinting." *J Chromatogr A* 1292, 219 (May 31, 2013) (10 pages).
Geesey, et al.; "Determination of bacterial growth and activity at solid-liquid interfaces," *Annu Rev Microbiol* 44, 579 (1990) (24 pages).
Solon, et al. "Fibroblast adaptation and stiffness matching to soft elastic substrates," *BiophysJ* 93, 4453 (Dec. 15, 2007) (9 pages).
Yu, et al. "Aflatoxin biosynthesis," *Rev Iberoam Micol* 19, 191 (Dec. 2002).
Roze, et al.; Compartmentalization and molecular traffic in secondary metabolism: a new understanding of established cellular processes, *Fungal Genet Biol* 48, 35 (Jan. 2011) (28 pages).
Rose "Ultrasonic waves in solid media," (Cambridge University Press, Cambridge ; New York, 1999), pp. xvi, 454 p. (22 pages).
Chanda et al.; "A key role for vesicles in fungal secondary metabolism," *Proc Natl Acad Sci U S A* 106, 1953 (Nov. 17, 2009) 7 pages.
Chanda, et al.; "A possible role for exocytosis in aflatoxin export in Aspergillus parasiticus," *Eukaryot Cell* 9, 1724 (Nov. 2010) (4 pages).
Falconer, et al.; "Biomass recycling and the origin of phenotype in fungal mycelia," *Proc Biol Sci* 272, 1727 (Aug. 22, 2005) (9 pages).

* cited by examiner

QUANTITATIVE ACOUSTIC CONTRAST TOMOGRAPHY FOR STUDYING FUNGAL GROWTH AND TOXICITY

The present application claims priority to U.S. Provisional Patent Application Ser. No. 61/924,928 titled "Quantitative Acoustic Contrast Tomography for Studying Fungal Growth and Toxicity" of Banerjee, et al. filed on Jan. 8, 2014, the disclosure of which is incorporated by reference herein.

BACKGROUND

Like many invasive cell-populations fungi need to fine-tune their mechanical and morphological properties, in response to different environmental signals, for pushing through their substrates to meet their metabolic and functional needs. Monitoring these properties in real-time in 3D is critical for identifying the molecular mechanisms that drive their invasions, and discovering novel modulatory molecules that change their invasiveness for the benefit of humans. Although light microscopy through its great progress in recent years has uncovered many local cellular events at nanometer resolution, visualizing global changes in morphology of cell colonies growing on and into their substrates with precision, is extremely challenging and often involves sample preparation that require cells to grow in conditions very different from their native growth conditions. Also mapping and quantifying mechanical properties of cell-populations in parallel with monitoring global morphology is very difficult because such properties cannot be visualized. The most popular methods to determine mechanical stress and viscoelastic properties within a micrometer or nanometer scale in live cells include localized aspiration of cytoplasm, magnetometry, and atomic force microscopy (AFM), where cells are perturbed by an external force and then the strains are mapped to determine the cell properties. However, for colonies with mostly non-synchronous metabolically diverse cells, as in fungal colonies, such local measurements will be incapable of providing an accurate reflection of the global morphomechanical behavior of the colony.

The goal that remains therefore, is a minimally-invasive technique that can provide accurate information of the mechanical and the morphological features of an entire landscape of a cell population.

SUMMARY

Objects and advantages of the invention will be set forth in part in the following description, or may be obvious from the description, or may be learned through practice of the invention.

Methods are generally provided for ultrasonically imaging a heterogeneous 3D-cell population without physically probing, where the cell population is positioned on a reflective surface to define an x,y plane having a thickness in a z-direction. In one embodiment, the method comprises: pulsing ultrasound waves having a wave frequency of about 10 MHz to about 2 GHz through a lens rod (e.g., about 50 MHz to about 300 MHz, such as about 85 MHz to about 115 MHz), wherein the lens rod focuses the ultrasound waves onto the cell population via a concave lens-head (e.g., comprising sapphire), and wherein the cell population is positioned on the reflective surface such that the ultrasound waves are reflected back to the lens-head; receiving the reflected waves through the lens head and the lens rod at a signal receiver; scanning the lens-head across multiple points in the x,y plane; and at each point in the x,y plane, moving the lens-head in a z-direction such that a signal is received at multiple intervals in the z-direction for each point in the x,y plane.

The reflective surface can have a uniform acoustic impedance that is higher than that of the cell population, such as on the order of about 3 times higher than that of the cell population. In most embodiments, a medium is positioned on the cell population, such as comprising water or air.

In one particular embodiment, pulsing ultrasound waves and receiving the reflected waves are both performed by a piezoelectric transducer. For instance, a switch can be electrically connected to the piezoelectric transducer, and the method can include toggling the switch such that an electrical connection is alternated from the piezoelectric transducer between a pulser and the signal receiver. In one embodiment, the switch operates at the pulsing frequency to pulse the ultrasound waves through the lens rod.

An ultrasonic imaging module is also generally provided. In one embodiment, the ultrasonic imaging module comprises: a pulser; a piezoelectric transducer configured to be activated using the pulser to generate ultrasound signals having wave frequencies between 10 MHz and 2 GHz; a lens rod attached to the piezoelectric transducer such that the ultrasound signals travel through the lens rod; a concave lens-head positioned within the lens rod and movable therein, wherein the concave lens-head is configured to focus the ultrasound signals traveling through the lens rod on a specimen positioned on a reflective surface; and a signal receiver attached to the piezoelectric transducer to receive reflected ultrasound signals from the specimen Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

The present disclosure is generally directed to a tri-modular acoustic contrast tomography for mapping, quantifying and correlating global fluctuations in mechanical and morphological properties derived simultaneously at multiple scales across invading fungal colonies as they expand on and into their substrates. The method, generally termed "quantitative acoustic contrast tomography" ("Q-ACT"), avoids any physical contact with specimens, and hence provides the most accurate readouts for studying mycelial invasion at a systems level during fungal pathogenesis. It has been demonstrated that the method could successfully extract and classify morphomechanical features from expanding colonies of a model fungal pathogen, *Aspergillus parasiticus*. As the colonies switched into their pathogenic mode upon the onset of secondary metabolism, they displayed unique signatures that were correlated with the release of the hepatocarcinogenic secondary metabolite, aflatoxin.

Q-ACT can offer a safe, rapid and powerful diagnostic framework for study of fungal pathogenesis in clinical and environmental samples by providing a critical read-out for the identification of in-cell molecular factors and antifungal therapeutics that modulate fungal invasion and pathogenicity. Introduction of air-coupled transducers in module 1 can significantly increase the functionality of the tomography by enabling detection of toxic mold growth inside humans, animals or crops without any need of painful biopsy or mechanical handling of the toxic samples.

In this method (FIG. 1), a piezoelectric transducer attached to a lens rod is activated using a pulser to generate broadband ultrasound signals (wave frequencies typically between 10 MHz and 2 GHz), which travels through the lens rod to focus the energy on the specimen via a concave lens-head. The entire spectrum of the reflected waves that comes back from the specimen to the lens-head finally travels back to the piezoelectric element, generating electrical signals that are recorded by a signal receiver. A necessary requirement for all these studies is an ultrasonic reflecting sheet beneath the specimen with uniform acoustic impedance that is higher than the specimen preferably in the order of about 3.

Fungal colonies and many other prokaryotic and eukaryotic cell populations however, are often cultured on soft solid substrates to mimic their behavior in their native growth environment. The colonies under these conditions grow in three dimensions, with non-uniform thickness. The acoustic properties of the substrates are predominantly non-uniform and depend on (a) the pattern of uptake of nutrients from the substrate by the cells, (b) the nature of material properties resulting from the invasion of the cells into the substrate, and (c) the release of metabolites from the cells into the substrate. As a result, such substrates display acoustic impedance values that are not only close to the values of the reflecting sheet but are largely non-uniform along the x,y plane. This makes ultrasonic imaging of colonies growing on soft substrates (like solid agar growth media or tissues) extremely challenging.

Figure 2:
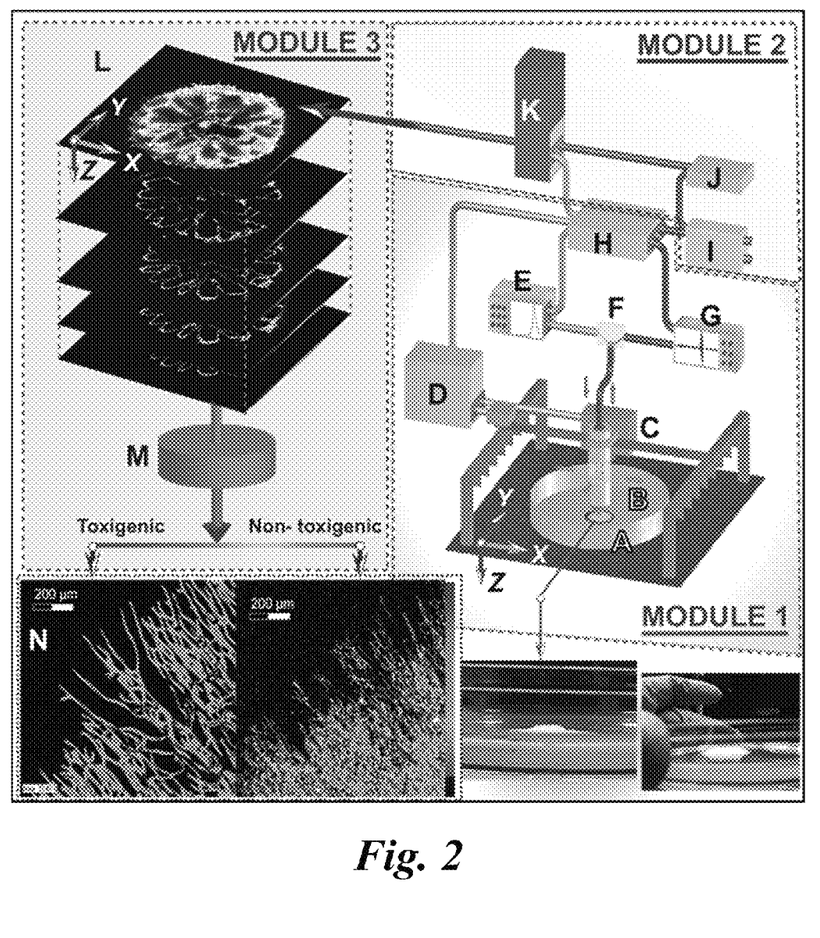
FIG. 2 shows a schematic representation of one particular embodiment of Q-ACT according to the present invention.

Here, a tri-modular acoustic tomography—a methodology is generally described that is termed "quantitative acoustic contrast tomography" (or "Q-ACT") with which these technical challenges can be successfully overcome. This method can derive global ultrasonic micrographs from a live colony of a model fungal pathogen, such as *Aspergillus parasiticus*, to simultaneously extract its mechanical and morphological features. *Aspergillus parasiticus* is one of the most well characterized fungal pathogens because it synthesizes and secretes a mycotoxin and hepatocarcinogen, aflatoxin, during secondary metabolism. The schematic representation of the method is shown in FIG. 2.

Figure 1:
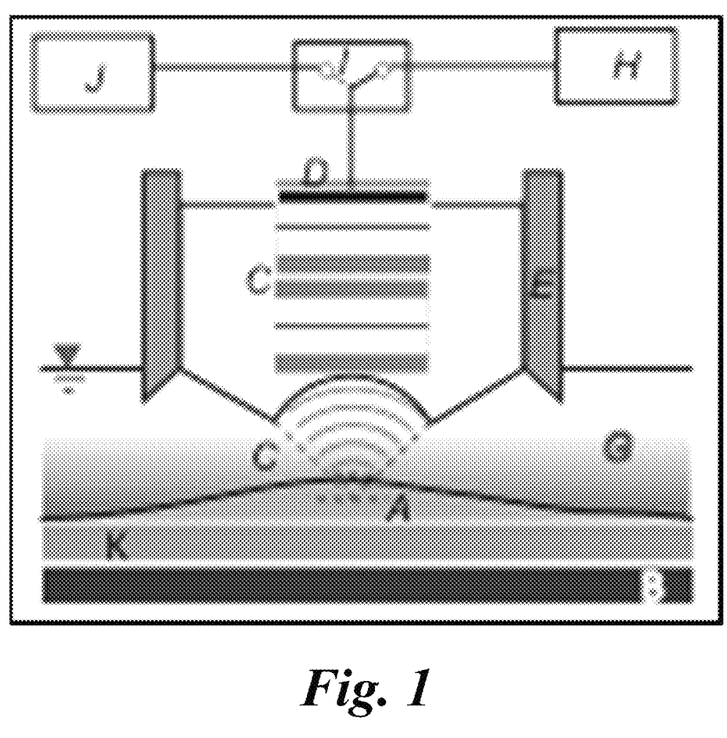
FIG. 1 shows an exemplary ultrasonic imaging according to an embodiment of the present invention.

Referring to FIG. 1, a specimen (A) is placed on a hard reflecting sheet (B) usually with an acoustic impedance higher than A (such as in the order of about 3), and is exposed to ultrasonic wide band (C) with frequencies typically ranging between 10 MHz and 2 GHz. The waves after emission from the piezoelectric transducer (D) travel through a sapphire lens rod protected with brass casing (E) and reach the specimen with a desired focusing angle after release from the concave lens head (F). The ultrasonic conducting medium (G), in most cases is water. Reflected waves from the specimen travels back to the piezoelectric transducer (D) after they are received at concave lens head (F) and are sent to the signal receiver (H). The switch (I) toggles between the pulser (J) and the signal receiver (H) during ultrasonic signal reception. As demonstrated in the Examples herein, Q-ACT overcame to two major technical challenges that hindered the compatibility of the system for imaging of fungal colonies: (i) their agar growth media (K) have acoustic impedance very similar to A and (ii) their colonies demonstrate large acoustic non-homogeneity even in the x,y planes for any depth.

Referring to module 1 of FIG. 2, the specimen (A), which is an *A. parasiticus* colony on an agar plate (amplified in the inset below) was exposed to a wideband ultrasonic frequency ranging from 50 MHz to 300 MHz emitted from an acoustic probe (B) with a custom designed lens head. Motor controllers (C) and (D) regulate the motion of the acoustic probe (B) in the z-direction (i.e., vertally) and the x,y plane. The switch (F) in co-ordination with the scanner (H), toggled the module between the ultrasonic emission mode governed by the pulser (E) and the signal reception mode, governed by signal receiver and display (G). Module 2 amplified the reflected ultrasonic signals in the signal amplifier (I) and decoded them to generate ultrasonic micrographs (L) using the real-time Hilbert filter (J) and the tomographic compiler (K). Module 3 extracted the morphomechanical information at hyphal and colony scales using the analytical domain (M) built with custom algorithms (see methods) and predicted the metabolic state of the colony—whether the fungus was toxigenic or non-toxigenic (N). Color bar in N, signifies the normalized total ultrasonic signal energy at every pixel point in the image.

Figure 3:
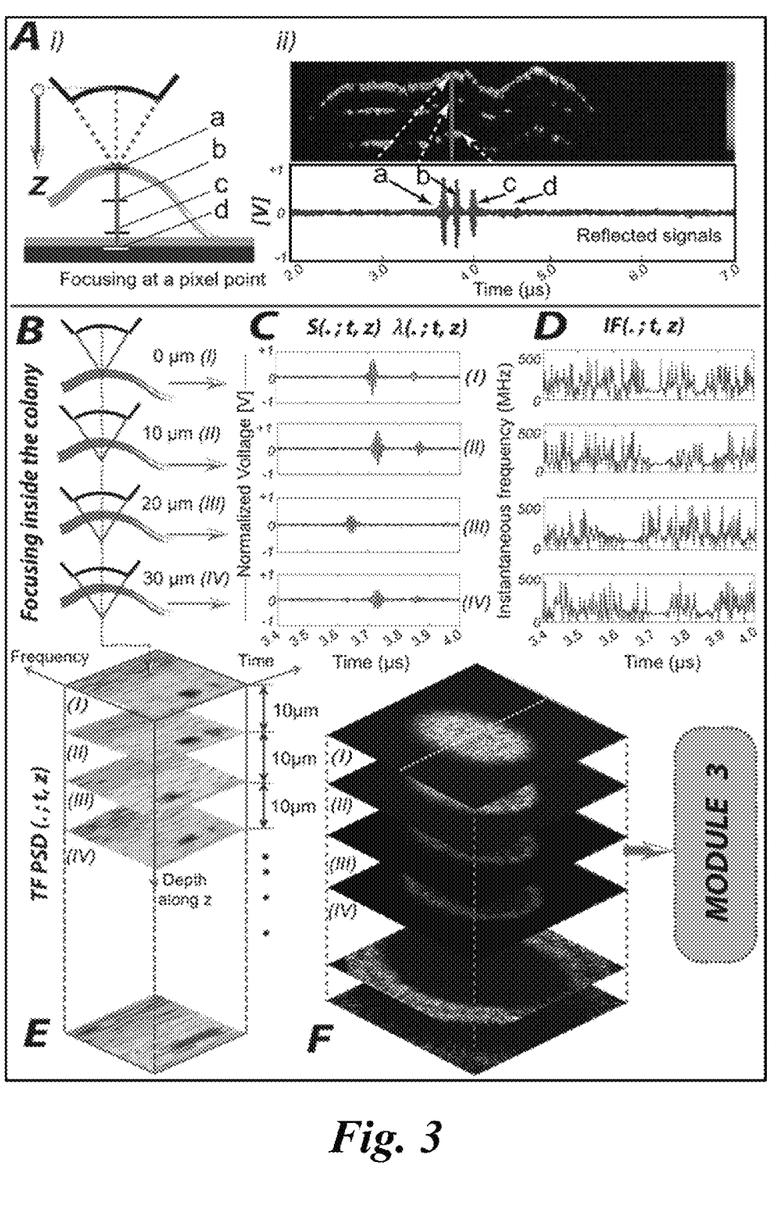
FIG. 3 shows the generation of the ultrasonic micrograph z-stacks from a sample *Aspergillus* colony, according to the Examples.

FIG. 3A shows (i) ultrasonic beams being focused at the top of the colony, and an exemplary scan performed at a pixel point along x,y plane. FIG. 3A also shows that (ii) depending on the relative position of lens head to the point of scan, transmitted and reflected waves interact differently at different points along the z axis e.g. wave interacted with the a, b, internal layers, c, colony-agar interface, d, agar-petri dish interface. FIG. 3B shows a diagram of xy scans performed at every 5 μm defocus distance along z axis. To demonstrate how transmitted and reflected waves interacted differently along z with the same x,y coordinates the first four defocus distances (i, ii, iii, iv) of a typical x,y coordinate, 10 μm apart are shown. FIG. 3C shows the time varying ultrasonic signal and time varying Hilbert amplitude at i, ii, iii, iv. FIG. 3D shows the instantaneous frequency obtained from real time Hilbert filter at i, ii, iii, iv. FIG. 3E shows the power spectral density of time frequency data obtained from instantaneous ultrasonic signals at i, ii, iii, iv.

FIG. 3F shows a typical example of the z-stacks of the ultrasonic micrographs over the entire xy plane at every 10 μm defocus distance.

Examples

Before sampling, an inoculum containing 104 spores of the wild type *A. parasiticus*, SU-1, was center-inoculated on an agar plate and grown in the dark at 30° C. The ultrasonic micrographs of the fungal colonies were obtained in module 1 (FIG. 2), referred to herein as the ultrasonic imaging module, where the colony was exposed to a panel of ultrasound waves with a wide range of frequencies. To obtain these micrographs, the colonies were covered with a thin layer (thickness of about 1000 μm) of water and placed inside an ultrasonic scanning chamber custom-designed to perform safe scan of the aflatoxin producing colonies and prevent any secreted aflatoxin from contaminating the equipment or the indoor air. By moving the ultrasonic lens along z-axis starting from an initialized preset defocus distance equal to the typical hyphal thickness (about 5 μm) we derived the maximum height from which we could send ultrasonic signals and receive the reflected signals from different depths of the specimen. For ultrasonic scanning, we chose a broadband ultrasound wave with dominant frequencies between about 50 MHz to about 300 MHz with maximum energy transmitted between about 85 MHz to about 115 MHz (peaked at about 100 MHz) based on our prior optimization experiments with *A. parasiticus* colonies. Frequencies lower than the selected band caused coarse resolution, which is unfit for decoding morphomechanical properties. Frequencies higher than the selected band lost contrast between the fungal cell and the agar due to their dispersive nature which result low acoustic impedance mismatch.

The reflected ultrasound signals from the surface and inside the colony and those traveling through the growth medium generated an array of temporal ultrasonic signatures from various pixel points within the volume of the colony. At different points at a particular depth across the xy plane, reflected ultrasonic beams interact with the colony differently (FIG. 3A). Depending on the position of the ultrasonic probe with respect to the colony they create longitudinal wave, shear wave, surface skimming longitudinal wave and Rayleigh waves that propagate back to the lens. Since conventional acoustic microscopy assumes homogeneity of specimens in z axis, decoding image data from any particular plane during 3D imaging of such acoustically non-homogeneous colonies is extremely difficult and involves loss of information on morphomechanical properties. Here we incorporated the acoustic non-homogeneity of the fungal specimens and their substrates by integrating a second module with module 1, for simultaneous convolution and subsequent de-convolution of the ultrasound signals that are reflected back from different depths of the colonies (FIG. 3B). Under module 2 (FIG. 2), also termed 'tomography compiler', we divided the total time domain signals of 2000 ns (ranging approximately between 2500 ns-4500 ns) obtained from module 1 into 100 segments of 20 ns each to obtain through spectral analysis, a) the time frequency (TF) signals (FIG. 3C-D) and b) a stack of TF power spectral density (TF PSD) plots (FIG. 3E) to determine the dominant frequencies at various pixel points across the colony volume. The signals collected from each pixel point in the volume of the colony were also summed across time at every pixel point (in x, y and z) described by a function $\Psi(.;z)$, where (.) signifies each pixel point on the xy plane. At every pixel points, the peak amplitudes of the frequency responses at central frequency 100 MHz that we call the $V(.;z)$ curves, were calculated after fast Fourier transform of the raw 4D time domain signals. Simultaneously using real time Hilbert transform of the 4D signals we next derived the instantaneous amplitude, phase and frequency data for all pixel points. Hence, the instantaneous ultrasonic wave reflected from any pixel point in the colony could be plotted in a 5-dimensional volume comprised of signal energy or $\Psi(.;z)$, $V(.;z)$, TF PSD expressed as $\phi(.;f,t,z)$, instantaneous amplitude expressed as $\lambda(.;t,z)$ and instantaneous frequency expressed as $IF(.;t,z)$. Here (.) denotes each pixel point on the xy plane, t denotes time, f denotes frequency and z denotes the depth of scanning inside the colony. In conjunction with module 1, we then optimized various parameters for ultrasonic scanning, such as coordinates of the pixels on xy plane, incremental depth of the lens along z direction, signaling time lag between scanner and the motor controller, switching time lag between pulser and receiver during acquiring signal at each pixel point, time taken by Hilbert filtering and tomography compiler module, to obtain the maximum speed of image acquisition with maximum resolution. The typical micrographs obtained after these optimizations are shown in FIG. 3F. The image resolution that we achieved was also a significant improvement over a conventional 100 MHz acoustic microscopy. Typical pixel size in xy plane was about 2 μm, when imaging individual hyphae (local scale) and about 20 μm, when imaging a complete colony.

Finally, we incorporated a third module (FIG. 2) that we call 'morphomechanical classifier' to: (a) uniquely quantify the global morphological features and mechanical strength profiles simultaneously in the colony, from the ultrasonic micrographs, using the module 2 generated 5D data of the instantaneous ultrasonic waves collected from the entire xyz space, and (b) correlate these features with the behavior of the pathogen at various times during its life cycle under different environmental conditions. Mechanical strength was mapped in the colony using the properties underlying wave reflection transmission phenomena across a multilayered solid media. Since mechanical strength at any given point can be expressed as a function of ultrasonic wave velocities at that point following Newton-Laplace equation for the speed of sound, we designed our custom algorithms within module 3, to process the entire 5D data set to render a map of instantaneous wave velocities at all points in the xyz space which could accurately reflect the strength profiles at every single voxel in the colony (mathematical details of processing of the 5D data set is discussed under methods).

Figure 4:
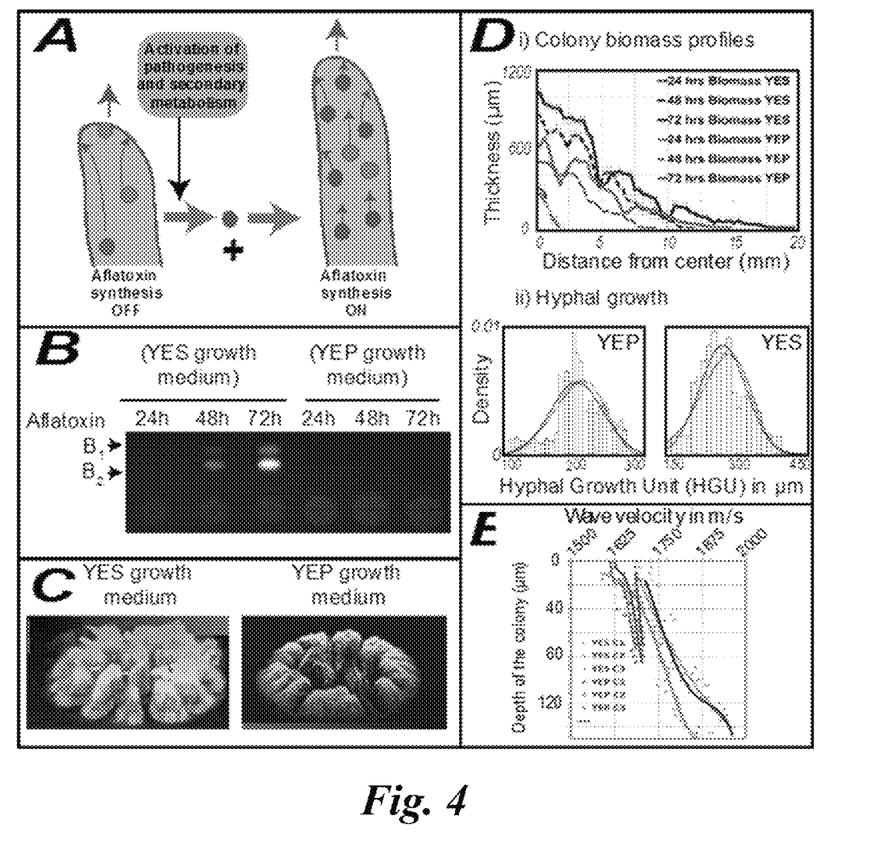
FIG. 4 shows the comparative Q-ACT of *A. parasiticus* colonies grown in aflatoxin inducing (YES agar) and non-inducing (YEP agar) growth conditions according to the Examples.

FIG. 4A shows a proposed model for enhanced hyphal wall biogenesis during aflatoxin synthesis. As the colonies initiate aflatoxin synthesis they up-regulate development of toxigenic vesicles. We hypothesized that an increased availability of wall materials on the hyphal surface due to higher secretion offered by the additional toxigenic vesicles would lead to higher hyphal growth rates, wall strengths and differential Q-ACTs between YES and YEP colonies. Green, secretory vesicles, Red, toxigenic vesicles, +, up-regulation B. Thin layer chromatograph demonstrating aflatoxin production by *A. parasitcus* only in YES agar at 48 h and 72 h after inoculation C. Comparative 3D projections of ultrasonic micrograph z-stacks of a 48 h YES and YEP colony D. Comparison of the morphology profiles extracted from the ultrasonic micrographs. i) colony biomass profiles of 24 h, 48 h and 72 h YES and YEP colonies, and, ii) distribution of HGU of YES and YEP colonies during the 72 h lifetime. E. Comparison of the hyphal strength profiles between YES and YEP colonies indicated by the distribution of ultrasonic wave velocity at different depths of the colonies. C1, C2 and C3 represent three different colonies for per growth medium.

We used Q-ACT to observe and quantify the morphomechanical changes that *A. parasiticus* colonies undergo as they switch to pathogenic mode and activate aflatoxin synthesis and secretion, a hallmark of their pathogenicity. Based on earlier studies that report a significant surge in the development of secretory vesicles that synthesize and secrete aflatoxin in toxigenic regions of the fungus, we hypothesized that an increased secretion during aflatoxin release at peak levels would result in increased availability of cell wall materials as well, leading to an increase in the average length of a hypha before branching out, expressed as hyphal growth unit (HGU) and the wall strength in the toxigenic regions (shown in the model in FIG. 4A).

We tested this hypothesis by conducting a time-course Q-ACT of SU-1 colonies grown in parallel, on yeast extract sucrose (YES) agar, a growth medium that activates aflatoxin biosynthesis and on yeast extract peptone (YEP) agar medium, which unlike YES does not activate aflatoxin synthesis (FIG. 4B). Upon observing a difference in gross macroscopic appearance of the colonies after 24 h, in the 3D-projections of ultrasonic micrograph z-stacks of YES and YEP (an example of 48 h colonies shown in FIG. 4C), we sought to quantify the changes in colony morphology and mechanical properties from the acoustic signatures of the colony using our custom algorithms of module 3. As shown in FIG. 4D, after 24 h we observed that unlike YEP colonies, YES colonies displayed a sharp increase in biomass profiles, that we express here as the thickness of the mycelia at different radial distances from the center of inoculation. Interestingly, for older colonies the thickness profiles of both YES and YEP colonies consistently (in five repeat experiments) displayed intermittent drops (FIG. 4D), implicating that instead of creating continuous structural framework, the fungus built their mycelial framework in concentric discrete circles, a phenomenon proposed and observed previously for filamentous fungi. Although the biological advantage for such architecture remains unclear at this point it is possible that such a structural framework might provide higher mechanical stability to the colony and enable better absorption of nutrients from the substrate.

We further proceeded to compute the probability distribution of HGU ($P_{HGU}$) between YES and YEP colonies. As a control, we also computed the probability distribution of the angles (HA) at which the hypha laterally branched out in each colonies ($P_{HA}$), which based on our hypothesis should be similar between YES and YEP colonies. As shown in FIG. 4E, $P_{HGU}$ of YES colonies demonstrated an average (±SD) of about 282 µm (±46 µm). In contrast, YEP colonies demonstrated an average $P_{HGU}$ (±SD) of about 201 µm (±39 µm). As we expected, PHA for both YES and YEP colonies showed an average (±SD) of about 37.5 (±11).

Finally, to test the hypothesis that the strength profiles of the hyphal walls change across the mycelium upon the onset of pathogenesis, we compared ultrasonic wave velocities in the entire mycelial volume in 48 h colonies, a time-point that corresponds to aflatoxin synthesis at peak levels (FIG. 4B). Comparison of the maps of instantaneous wave velocities in the YES and YEP colonies revealed a higher increase of velocities with colony depth in YES colonies (about 1.65 Km/sec to about 1.92 KM/sec) compared to YEP colonies (about 1.59 Km/sec to about 1.7 KM/sec) (FIG. 4E), implicating that compared to YEP colonies, YES colonies display a higher increase in hyphal strength at depths closer to the substrate. These results suggest that increased mycelial strength profiles in YES colonies lead to higher biomass profiles (FIG. 4C) and higher $P_{HGU}$ (FIG. 4D), implicating higher mycelial invasion compared to the YEP colonies. To test whether substrate material properties could contribute to such a difference in invasion levels as well, we measured ultrasonic wave velocities in YES and YEP medium. We observed that wave velocities do not demonstrate any significant difference in either media (about 1.62±0.08 Km/sec for YES medium and ~1.65±0.06 Km/sec for YEP medium) suggesting that both media provide approximately equal resistance to the mycelia during invasion.

It is to be understood that the use of "comprising" herein specifically discloses and includes the embodiments that "consist essentially of" the named components (i.e., contain the named components and no other components that significantly adversely affect the basic and novel features disclosed), and embodiments that "consist of" the named components (i.e., contain only the named components except for contaminants which are naturally and inevitably present in each of the named components).

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of ultrasonically imaging a heterogeneous 3D-cell population without physically probing, the cell population positioned on a reflective surface to define an x,y plane having a thickness in a z-direction, the method comprising:
    pulsing ultrasound waves having a wave frequency of about 10 MHz to about 2 GHz through a lens rod, wherein the lens rod focuses the ultrasound waves onto the cell population via a concave lens-head, and wherein the cell population is positioned on the reflective surface such that the ultrasound waves are reflected back to the lens-head;
    receiving the reflected waves through the lens head and the lens rod at a signal receiver;
    scanning the lens-head across multiple points in the x,y plane; and
    at each point in the x,y plane, moving the lens-head in a z-direction such that a signal is received at multiple intervals in the z-direction for each point in the x,y plane.

2. The method of claim 1, wherein the reflective surface has a uniform acoustic impedance that is higher than that of the cell population.

3. The method of claim 2, wherein the uniform acoustic impedance is on the order of about 3 times higher than that of the cell population.

4. The method of claim 1, wherein a medium is positioned on the cell population.

5. The method of claim 4, wherein the medium comprises water.

6. The method of claim 4, wherein the medium comprises air.

7. The method of claim 1, wherein the ultrasound waves have a wave frequency of about 50 MHz to about 300 MHz.

8. The method of claim 1, wherein the ultrasound waves have a wave frequency of about 85 MHz to about 115 MHz.

9. The method of claim 1, wherein the lens comprises sapphire.

10. The method of claim 1, wherein pulsing ultrasound waves and receiving the reflected waves are both performed by a piezoelectric transducer.

11. The method of claim 10, wherein a switch is electrically connected to the piezoelectric transducer.

12. The method of claim 11, further comprising:
toggling the switch such that an electrical connection is alternated from the piezoelectric transducer between a pulser and the signal receiver.

13. The method of claim 12, wherein the ultrasound waves are pulsed at a pulse frequency, and wherein the switch operates at the pulsing frequency to pulse the ultrasound waves through the lens rod.

* * * * *